US009290423B2

(12) United States Patent
Trewella et al.

(10) Patent No.: US 9,290,423 B2
(45) Date of Patent: *Mar. 22, 2016

(54) PROCESS OF GENERATING A RENEWABLE BIOFUEL FROM A HYDROTREATED STREAM OF CONDENSED OXYGENATES

(71) Applicant: KiOR, Inc., Pasadena, TX (US)

(72) Inventors: Jeffrey C Trewella, Kennett Square, PA (US); Edward J Smith, Houston, TX (US); Vicente Sanchez, Houston (ES); Brent Moore, Friendswood, TX (US); Stephen J. McGovern, Mantua, NJ (US)

(73) Assignee: KiOR, LLC, Pasadena, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/681,145

(22) Filed: Nov. 19, 2012

(65) Prior Publication Data

US 2014/0142354 A1    May 22, 2014

(51) Int. Cl.
*C07C 1/24* (2006.01)
*C10G 3/00* (2006.01)

(52) U.S. Cl.
CPC ... *C07C 1/24* (2013.01); *C10G 3/50* (2013.01); *C10G 2300/1011* (2013.01); *C10G 2300/1037* (2013.01); *Y02P 30/20* (2015.11)

(58) Field of Classification Search
CPC .... C07C 1/24; C10G 3/50; C10G 2300/1011; C10G 2300/1037
USPC ......................................................... 585/310
See application file for complete search history.

(56) References Cited

U.S. PATENT DOCUMENTS

| 4,344,770 | A | | 8/1982 | Capener et al. | |
|---|---|---|---|---|---|
| 4,384,153 | A | * | 5/1983 | Dessau | 585/366 |
| 4,686,317 | A | | 8/1987 | Quann | |
| 5,504,259 | A | | 4/1996 | Diebold et al. | |
| 5,763,716 | A | | 6/1998 | Benham et al. | |
| 7,671,246 | B2 | | 3/2010 | Dumesic et al. | |
| 8,075,642 | B2 | | 12/2011 | Dumesic et al. | |
| 8,143,469 | B2 | | 3/2012 | Koivusalmi et al. | |
| 2007/0225383 | A1 | | 9/2007 | Cortright et al. | |
| 2009/0069607 | A1 | * | 3/2009 | Smith et al. | 568/671 |
| 2010/0312028 | A1 | | 12/2010 | Olson | |
| 2011/0094147 | A1 | | 4/2011 | Bartek et al. | |

(Continued)

FOREIGN PATENT DOCUMENTS

| WO | WO2007103858 | | 9/2007 |
|---|---|---|---|
| WO | WO2007103858 | A2 | 9/2007 |
| WO | WO2010033789 | A2 | 3/2010 |

OTHER PUBLICATIONS

Paula A. Zapata, et al.; Condensation/Hydrogenation of Biomass-Derived Oxygenates in Water/Oil Emulsions Stabilized by Nanohybrid Catalysts; Topics in Catalysis, ISSN 1022-5528, vol. 55, Combined 1-2.

*Primary Examiner* — In Suk Bullock
*Assistant Examiner* — Philip Louie
(74) *Attorney, Agent, or Firm* — John Wilson Jones; Jones & Smith, LLP

(57) ABSTRACT

A renewable fuel may be obtained from a bio-oil containing $C_3$-$C_5$ oxygenates. In a first step, the bio-oil is subjected to a condensation reaction in which the oxygenates undergo a carbon-carbon bond forming reaction to produce a stream containing $C_6$+ oxygenates. In a second step, the stream is hydrotreated to produce $C_6$+ hydrocarbons.

24 Claims, 2 Drawing Sheets

(56) References Cited

U.S. PATENT DOCUMENTS

| | | |
|---|---|---|
| 2011/0245554 A1 | 10/2011 | Huber et al. |
| 2011/0283601 A1 | 11/2011 | Ditsch |
| 2011/0296745 A1 | 12/2011 | Hilten et al. |
| 2012/0022307 A1 | 1/2012 | Yanik et al. |
| 2012/0137572 A1 | 6/2012 | Bartek et al. |
| 2012/0172643 A1 | 7/2012 | Ramirez Corredores et al. |
| 2013/0036660 A1* | 2/2013 | Woods et al. .......... 44/307 |
| 2013/0237728 A1 | 9/2013 | Lotero |
| 2014/0142355 A1 | 5/2014 | Bauer et al. |

* cited by examiner

PROCESS OF GENERATING A RENEWABLE BIOFUEL FROM A HYDROTREATED STREAM OF CONDENSED OXYGENATES

FIELD OF THE INVENTION

The invention relates to a process of generating a renewable biofuel from biomass converted liquids containing $C_3$ to $C_5$ oxygenates by first subjecting the $C_3$ to $C_5$ oxygenates to a carbon-carbon bond forming condensation reaction and then hydrotreating the resulting $C_6$+ oxygenates.

BACKGROUND OF THE INVENTION

Renewable energy sources, such as biofuels, provide a substitute for fossil fuels and a means of reducing dependence on petroleum oil. In light of its low cost and wide availability, biomass is often used as a feedstock to produce pyrolysis oil (which is relatively soluble in water) or bio-oil which, in turn, is used to produce biofuel.

Many different conversion processes have been developed for converting biomass to bio-oil or pyrolysis oil. Existing biomass conversion processes include, for example, combustion, gasification, slow pyrolysis, fast pyrolysis, liquefaction and enzymatic conversion. Pyrolysis oil is the resultant of thermal non-catalytic treatment of biomass. The thermocatalytic treatment of biomass renders liquid products that spontaneously separate into an aqueous phase and an organic phase. Bio-oil consists of the organic phase. Pyrolysis oil and bio-oil may be processed into transportation fuels as well as into hydrocarbon chemicals and/or specialty chemicals.

While thermolysis processes and other conversion processes produce high yields of such oils, much of the pyrolysis oil and bio-oil produced is of low quality due to the presence of high levels of low molecular weight oxygenates having 5 or less carbon atoms ($C_5$—). Such low MW oxygenates can be in alcohols, aldehydes, ketones, carboxylic acids, glycols, esters, and the like. Those having an isolated carbonyl group include aldehydes and ketones like methyl vinyl ketone and ethyl vinyl ketone.

Such oils thus require secondary upgrading in order to be utilized as drop-in oxygen free transportation fuels due to the high amounts of such oxygenates. A known method for converting oxygenates into hydrocarbons is hydrotreating wherein the stream is contacted with hydrogen under pressure and at moderate temperatures, generally less than 750° F., over a fixed bed reactor.

Transportations fuels predominately contain hydrocarbons having six or more carbon atoms ($C_6$+) (though small amounts of $C_5$— hydrocarbons are present in some gasolines). Thus, hydrocarbons derived by hydrotreating $C_5$— oxygenates are of little value in transportation fuels. Additionally, hydrotreating $C_5$— oxygenates consumes valuable hydrogen in the reactor. Thus, the efficiency of secondary upgrading of pyrolysis oil and bio-oil is compromised by the presence of the $C_5$— oxygenates.

Alternative processes have therefore been sought for enhancing the efficiency in hydrotreating of oils derived from biomass. Processes for enhancing the yield of hydrotreated pyrolysis oil and bio-oil from streams containing $C_5$— oxygenates, especially $C_3$ to $C_5$ oxygenates, have been sought.

SUMMARY OF THE INVENTION

The invention is drawn to a process for treating pyrolysis oil or bio-oil wherein carbonyl containing $C_3$ oxygenates, $C_4$ oxygenates and $C_5$ oxygenates and mixtures of such oxygenates are subjected to a condensation reaction prior to subjecting the oil to hydrotreatment. The condensation reaction forms carbon-carbon bonds to produce $C_6$+ oxygenates which are subsequently hydrotreated to $C_6$+ hydrocarbons.

The yield of hydrotreated oil from the pyrolysis oil stream or bio-oil stream may be enhanced by subjecting the carbonyl containing $C_3$-$C_5$ oxygenates in a pyrolysis oil or bio-oil stream to a carbon-carbon bond forming condensation reaction and then hydrotreating the resulting condensate(s).

In an embodiment, a renewable biofuel may be produced from a pyrolysis oil or bio-oil feedstream by first subjecting the carbonyl containing $C_3$-$C_5$ oxygenates in the oil to a carbon-carbon bond forming condensation reaction. The resulting stream is then introduced into a hydrotreater to produce a hydrotreated feedstream. A renewable biofuel may be rendered from the hydrotreated feedstream. For instance, a renewable fuel may be prepared by combining the hydrotreated stream with a liquid hydrocarbon obtained from a refinery stream.

In another embodiment, a renewable biofuel may be produced from a hydrotreated pyrolysis oil or bio-oil by first feeding the stream to a condensation reactor, such as a distillation column, and then subjecting the $C_3$-$C_5$ oxygenates in the stream to a carbon-carbon bond forming condensation reaction followed by hydrotreating the resulting condensates. The hydrotreated condensates may then be subjected to fractionation to render a $C_6$+ naphtha fraction having a final boiling point below about 420° F.

In still another embodiment, a renewable biofuel may be produced from biomass by first separating a predominately liquid phase containing $C_3$-$C_5$ oxygenates from a treated biomass, forming condensates through a carbon-carbon bond forming reaction from the higher MW oxygenate condensates, and then hydrotreating the condensates.

In yet another embodiment, the hydrotreated condensates may be subjected to fractionation to render separate hydrocarbon fractions containing (i) $C_5$, $C_6$, $C_7$ and $C_8$ hydrocarbons and (ii) $C_9$+ hydrocarbons.

In addition, transportation fuels may be prepared from the resulting separated hydrocarbon fractions.

In another embodiment, the hydrotreated condensates are separated into a naphtha fraction containing predominately $C_6$, $C_7$, $C_8$, $C_9$, and $C_{10}$ hydrocarbons and a hydrocarbon fraction containing $C_{11}$+ hydrocarbons.

The $C_3$-$C_5$ oxygenates may include carbonyl containing moieties including carboxylic acids, esters, ketones and/or aldehydes.

In an embodiment, the carbon-carbon bond forming condensation reaction consists of a Diels-Alder reaction.

In another embodiment, the carbon-carbon forming condensation reaction consists of an aldol condensation reaction.

In another embodiment, the carbon-carbon forming condensation reaction consists of a Robinson annulation reaction.

In yet another embodiment, the condensation of the $C_3$-$C_5$ oxygenates may occur in a distillation column. A heterogeneous acid catalyst may be present in the distillation column. Preferred heterogeneous acid catalysts may include natural or synthetic zeolites, sulfonated resins (such as sulfonated polystyrene, sulfonated fluoropolymers, sulfonated fluorocopolymers), sulfated zirconia, chlorided alumina, and amorphous SiAl.

BRIEF DESCRIPTION OF THE DRAWINGS

In order to more fully understand the drawings referred to in the detailed description of the present invention, a brief description of each drawing is presented, in which.

DETAILED DESCRIPTION OF THE PREFERRED EMBODIMENTS

The yield of $C_6+$ hydrocarbons from pyrolysis oil or bio-oil may be increased by the process defined herein. The process consists of two principal steps. In the first step, low value carbonyl containing $C_3$, $C_4$, and $C_5$ oxygenates within the stream are converted to heavier ($C_6+$) oxygenates in a condensation reactor. In the second step of the process, the heavier oxygenates are hydrotreated to render the $C_6+$ hydrocarbons.

Figure 1:
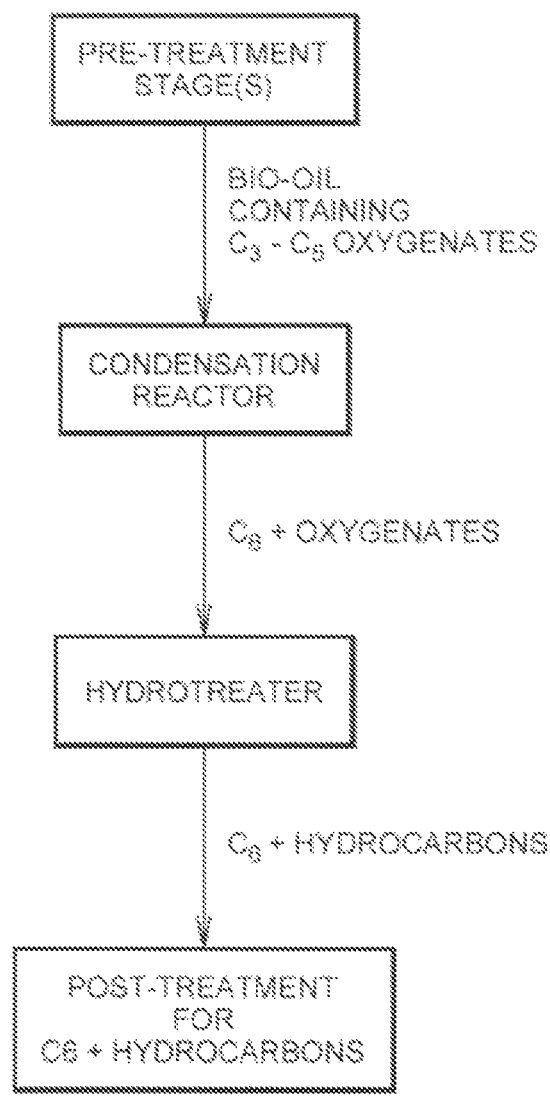
FIG. 1 is a schematic diagram of a representative process defined herein wherein a biomass derived stream is condensed prior to introduction into a hydrotreater.

FIG. 1 is a flow diagram wherein bio-oil or pyrolysis oil containing $C_3$-$C_5$ oxygenates is introduced into a condensation reactor prior to treatment of the stream with hydrogen in the hydrotreater. (Shale oil produced by pyrolysis, hydrogenation or thermal dissolution shall be included within the term "pyrolysis oil" as used herein.) The amount of water in the stream introduced into the conversion reactor is typically no greater than 40 volume percent, more typically less than 10 volume percent.

Prior to entering the condensation reactor, the biomass may be subjected to a pre-treatment operation. After condensation of at least some of the $C_3$-$C_5$ oxygenates, $C_6+$ oxygenates are then introduced into a hydrotreater where the condensed bio-oil mixture is subjected to deoxygenation by the introduction of hydrogen. Typically from 90 to about 99.99% of the oxygen is removed from the oxygenates in the hydrotreater. Typically, the oxygen complexes with hydrogen in the hydrotreater to form water which is decanted from the predominately hydrocarbon hydrotreated oil in the back of the hydrotreater unit. The oil stream exiting the hydrotreater is thereby enriched in $C_6+$ hydrocarbons.

The condensation reaction product consisting of a $C_6+$ oxygenates is produced by a carbon-carbon bond forming reaction between two or more $C_3$-$C_5$ oxygenates. It is possible for any two molecules of carbonyl containing $C_3$-$C_5$ oxygenates to react with each other. Thus, any such $C_3$ oxygenate, for example, may react with one or more such oxygenates selected from $C_3$ oxygenates, $C_4$ oxygenates or $C_5$ oxygenates; any such $C_4$ oxygenate may react with one or more any such oxygenates selected from $C_3$ oxygenates, $C_4$ oxygenates or $C_5$ oxygenates; and any such $C_5$ oxygenate may react with one or more any such oxygenates selected from $C_3$ oxygenates, $C_4$ oxygenates or $C_5$ oxygenates. In addition, any $C_3$ oxygenate, $C_4$ oxygenate or $C_5$ oxygenate may react with one or more oxygenates having carbon content in excess of $C_5$. For example, a $C_3$ oxygenate may react with a $C_7$ oxygenate; a $C_3$ oxygenate may react with a $C_4$ oxygenate and a $C_7$ oxygenate; a $C_3$ oxygenate may react with another a $C_3$ oxygenate, a $C_4$ oxygenate and a $C_7$ oxygenate; etc.

The oxygenates may be converted to higher molecular weight oxygenates in any reactor which affects carbon carbon bond formation. Suitable reactors may include a fixed bed reactor, a continuous stirred tank reactor (CSTR), a distillation column, a catstill (catalytic distillation unit) a stripper, as well as a heat exchanger.

The condensation products may be further processed by hydrotreating to provide renewable transportation fuels. In a preferred embodiment, the mixture exiting the condensation reactor is deoxygenated in a hydrotreater having a catalytic hydrotreating bed.

Alternatively, the renewable fuel may be blended with a petroleum-derived fuel to produce a blended renewable fuel. For example, the renewable fuel may be blended with a petroleum-derived gasoline in an amount of at least 0.01 to no more than 50 weight percent, including from about 1 to 25 weight percent and further including from about 2 weight percent to 15 percent by weight, of the petroleum-derived gasoline to produce a blended, partially-renewable gasoline. In addition, the renewable fuel may be blended with a petroleum-diesel to produce a blended, partially-renewable diesel fuel in an amount of at least 0.01 to no more than 50 weight percent, including from about 1 to 25 weight percent and further including from about 2 weight percent to 15 percent by weight, of the petroleum-derived diesel. Further, the renewable fuel may be blended with a petroleum-derived fuel oil in an amount of at least 0.01 to no more than 50 weight percent, including from about 1 to 25 weight percent and further including from about 2 weight percent to 15 percent by weight, of the petroleum-derived fuel oil.

The pyrolysis oil or bio-oil containing $C_3$-$C_5$ oxygenates may originate from the treatment of biomass in a biomass conversion reactor. Biomass may be in the form of solid particles. The biomass particles can be fibrous biomass materials comprising cellulose. Examples of suitable cellulose-containing materials include algae, paper waste, and/or cotton linters. In one embodiment, the biomass particles can comprise a lignocellulosic material. Examples of suitable lignocellulosic materials include forestry waste such as wood chips, saw dust, pulping waste, and tree branches; agricultural waste such as corn stover, wheat straw, and bagasse; and/or energy crops such as eucalyptus, switch grass, and coppice. The biomass may be in a solid or finely divided form or may be a liquid. Typically, the water soluble content of the biomass is no greater than about 7 volume percent.

The biomass may be thermocatalytically treated to render bio-oil or may be thermally treated (non-catalytically) to produce pyrolysis oil. Either the bio-oil or the pyrolysis oil may be subjected to any number of conventional treatments prior to being introduced into the condensation reactor. For instance, the liquid phase of the bio-oil or pyrolysis oil may be separated from the solids in a solids separator. The oil may then be purified, partially purified or non-purified and may be produced within the same plant or facility where the renewable biofuel is prepared or may be produced in a remote location. Further, the stream subjected to the condensation reactor may have been produced within the same plant or facility in which the hydrotreater is located. In addition, the biomass may have been treated in the same plant or facility where the renewable biofuel is prepared or produced in a remote location.

Figure 2:
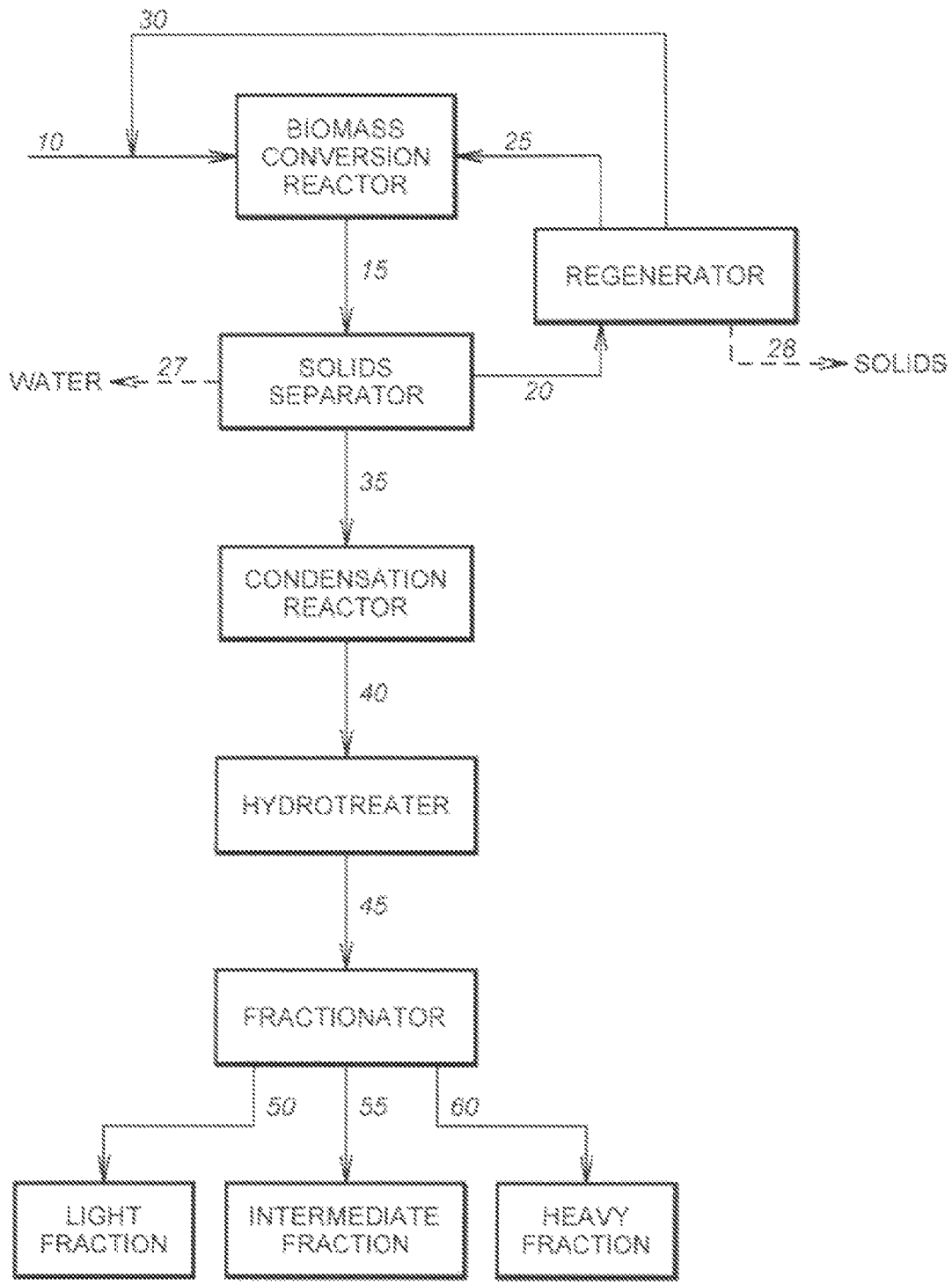
FIG. 2 is a schematic diagram of a representative process using the inventive steps defined herein.

Exemplary treatment stages are illustrated in FIG. 2 and any number of permutations may be used in the process described herein. For example, biomass particles may be prepared from biomass sources and larger particles by techniques such as milling, grinding, pulverization, and the like. The biomass may also be dried by methods known to those skilled in the art.

Referring, for example, to FIG. 2, biomass may be introduced via line 10 into a biomass conversion unit and be subjected to thermal pyrolysis, catalytic gasification, thermocatalytic conversion, hydrothermal pyrolysis, or another biomass conversion process. Biomass conversion unit may include, for example, a fluidized bed reactor, a cyclone reactor, an ablative reactor, or a riser reactor. In a biomass conversion unit, solid biomass particles may be agitated, for example, to reduce the size of particles. Agitation may be facilitated by a gas including one or more of air, steam, flue gas, carbon dioxide, carbon monoxide, hydrogen, and hydrocarbons such as methane. The agitator further be a mill (e.g., ball or hammer mill) or kneader or mixer.

FIG. 2 further shows that effluent from the biomass conversion unit may be introduced into a solids separator via line 15. Suitable separators may include any conventional device capable of separating solids from gas and vapors such as, for example, a cyclone separator or a gas filter.

In addition to the removal of heavy materials and solids, water may be removed during the separation at 27. For instance, during an aldol reaction, water may be removed during separation. There must a density difference between the water and oil in order for the water and oil to separate in the separator.

Solid particles recovered in solids separator may further be introduced into a regenerator via line 20 for regeneration, typically by combustion. After regeneration, at least a portion of the hot regenerated solids may be introduced directly into biomass conversion reactor via line 25. Alternatively or additionally, the hot regenerated solids via line 30 may be combined with biomass prior to introduction of biomass into biomass conversion reactor or may be purged from the regenerator via line 28.

Bio-oil or pyrolysis oil, having the solids removed is then introduced into the condensation reactor via line 35. The bio-oil or pyrolysis oil stream typically has an oxygen content in the range of 10 to 50 weight percent and a high percentage of $C_3$-$C_5$ oxygenates. Typically, from about 1 to about 25 weight percent of the bio-oil contains $C_3$-$C_5$ oxygenates. Such oxygenates may contain carboxylic acids, carboxylic acid ester, ketones (such as methyl vinyl ketone and ethyl vinyl ketone) as well as aldehydes.

The mixture exiting the condensation reactor may then be introduced into the hydrotreating unit via line 40 where the mixture is subjected to deoxygenation by the introduction of hydrogen. Hydrocarbons, water, and other by-products, such as hydrogen sulfide, are formed in the hydrotreatment operation. Prior to introduction into the hydrotreater the mixture exiting the condensation reactor having been enriched in $C_6$+ oxygenates may be subjected to conventional treatments.

Subsequent to producing hydrocarbons in the hydrotreater, the hydrotreated stream may be subjected to any number of conventional post-hydrotreated treatments.

For instance, as illustrated in FIG. 2, all or a portion of the hydrocarbon stream may be introduced into a fractionator via line 45. In the fractionator, at least a portion of the material may be separated through line 50 as light fraction, line 55 as an intermediate fraction, and line 60 as a heavy fraction. The light fraction may have a boiling range below petroleum-derived gasoline and the intermediate fraction may have a boiling range comparable to petroleum-derived gasoline. The heavy fraction may have a boiling range comparable to diesel fuel. For instance, in an embodiment, the light fraction may have a boiling point between from about 150° F. to about 180° F., the intermediate fraction may have a boiling point between from about 180° F. to about 420° F. and the heavy fraction may have a boiling point above 420° F.

The building of carbon-carbon bonds in the condensation reactor to form $C_5$+ hydrocarbons may progress via an enol or enolate addition to a carbonyl compound. Suitable reactions may include an aldol condensation or Michael addition reaction or a mixture thereof. In addition, the building of carbon-carbon bonds in the condensation reactor may proceed by a cycloaddition reaction wherein two or more independent pi-electron systems form a ring. Suitable cycloaddition reactions may include a Diels Alder reaction, a Robinson annulation reaction as well as mixtures thereof. These reactions can proceed via a base catalyzed anionic reaction mechanism or an acid catalyzed cationic reaction mechanism.

In a preferred embodiment, the cycloaddition reaction is a Diels Alder reaction wherein a conjugated diene or conjugated enone is reacted with a dienophile to render a cyclohexene or a dihydropyran or substituted cyclohexene ring or substituted a dihydropyran. A low molecular weight compound having an electron withdrawing group within the bio-oil or pyrolysis oil may function as the dienophile. Typically, the dienophile is a vinylic ketone or vinylic aldehyde represented by the $C_3$-$C_5$ oxygenates of the bio-oil. A vinylic ketone or vinylic aldehyde can also serve as the conjugated enone. A representative reaction scheme of a Diels-Alder reaction followed by hydrotreating wherein light hydrocarbons are converted to heavy hydrocarbons may be represented as follows:

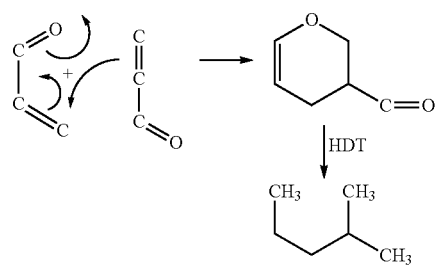

Further, the formation of $C_5$+ hydrocarbons may proceed by an aldol condensation reaction. A representative aldol condensation reaction may be represented by the following schematic pathway wherein an enol or an enolate ion reacts with an aldehyde or a ketone to form either a β-hydroxyaldehyde or a β-hydroxyketone:

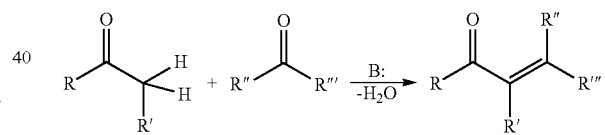

wherein R, R', R" and R'" are each independently selected from the group consisting of hydrogen, hydroxy, $C_1$-$C_8$ alkyl, alkenyl, and cycloalkyl, $C_1$-$C_{10}$ mono- and bicyclic aromatic and heterocyclic moieties (including heterocyclic groups derived from biomass), and carbonyls and carbohydrates such as ethanedione, glyceraldehyde, dihydroxyacetone, aldotetroses, aldopentoses, aldohexoses, ketotetroses, ketopentoses, ketohexoses, etc., provided that both R" and R'" are not hydrogen. The reaction can also proceed via an acid catalyzed cationic reaction mechanism.

The aldol condensation reaction may be a Claisen-Schmidt condensation reaction between a ketone and a carbonyl compound lacking an alpha hydrogen wherein an enolate ion typically is added to the carbonyl group of another, un-ionized reactant.

The reaction of carbonyl containing $C_5$— oxygenates in the condensation reactor may further proceed by a Michael addition wherein the carbonyl oxygenate undergoes a 1,4 addition to an enol or enolate anion.

Further, the $C_5$+ hydrocarbons may be formed by a ring formation reaction such as a Robinson annulation reaction between a ketone containing a α-$CH_2$ group and a α,β-unsaturated carbonyl (like methyl vinyl ketone). In a Robinson annulation reaction, an enolate executes a Michael addition to the α,β-unsaturated carbonyl compound. This is followed by an intramolecular aldol reaction to form the keto alcohol by an aldol ring closure followed by dehydration. Representative Robinson annulations reactions include:

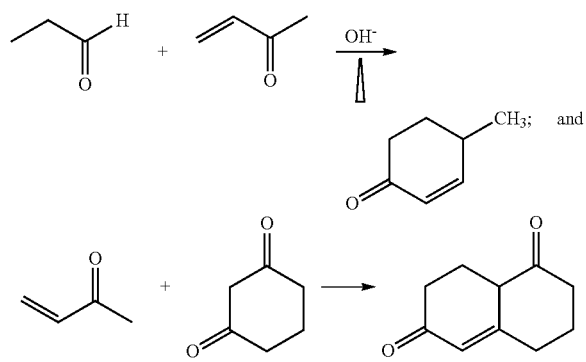

In both of these illustrated reactions, a deprotonated ketone acts as a nucleophile in a Michael reaction on a vinyl ketone to produce a Michael adduct prior to the aldol condensation reaction. The reaction can also proceed via an acid catalyzed cationic reaction mechanism.

Condensation occurs in the condensation reactor in the presence of heat. Typically, the condensation reactor is heated to a temperature from about 230° F. to about 450° F. The reaction may be promoted and/or facilitated by the presence of a base catalyst or an acid catalyst and preferably heterogeneous acid catalysts.

In a preferred embodiment, condensation occurs by catalytic distillation wherein the catalyst is placed within the condensation reactor in areas where concentrations of reactants are elevated.

Suitable homogeneous acid catalysts are selected from the group consisting of inorganic acids (such as sulfuric acid, phosphoric acid, hydrochloric acid and nitric acid); trifluoroacetic acid; organic sulfonic acids (such as p-toluene sulfonic acid, benzenesulfonic acid, methanesulfonic acid, trifluoromethanesulfonic acid, 1,1,2,2-tetrafluoroethanesulfonic acid, 1,2,3,2,3,3-hexapropanesulfonic acid); perfluoroalkylsulfonic acids, and combinations thereof. Often, the pKa of the organic acid is less than 4. Also suitable are metal sulfonates, metal sulfates, metal trifluoroacetates, metal triflates, such as bismuth triflate, yttrium triflate, ytterbium triflate, neodymium triflate, lanthanum triflate, scandium triflate, zirconium triflate, and zinc tetrafluoroborate.

In a preferred embodiment, a heterogenous acid catalyst is used such as a natural or synthetic zeolite, sulfonated resin (such as sulfonated polystyrene, sulfonated fluoropolymers, sulfonated fluorocopolymers), sulfated zirconia, chlorided alumina, or amorphous SiAl or a mixture thereof.

Exemplary zeolites include those of the ZSM-type, including ZSM-5 (as disclosed in U.S. Pat. No. 4,490,566)) and zeolite beta (disclosed in U.S. Pat. No. 4,490,565).

Perfluorinated ion exchange polymers (PFIEP) containing pendant sulfonic acid, carboxylic acid, or sulfonic acid and carboxylic acid groups may also be used.

In a preferred embodiment, the acid catalyst is a fluorinated sulfonic acid polymers which may be partially or totally converted to the salt form. Such products include those polymers having a perfluorocarbon backbone and a pendant group represented by the formula —$OCF_2CF(CF_3)OCF_2CF_2SO_3X$, wherein X is H, an alkali metal or $NH_4$. Polymers of this type are disclosed in U.S. Pat. No. 3,282,875.

One particularly suitable fluorinated sulfonic acid polymer is Nafion® perfluorinated sulfonic acid polymers of E.I. du Pont de Nemours and Company. Such polymers include those of a tetrafluoroethylene backbone having incorporated perfluorovinyl ether groups terminated with sulfonate groups. Exemplary of such copolymers are Nafion-H and Nafion® Super Acid Catalyst, a bead-form strongly acidic resin which is a copolymer of tetrafluoroethylene and perfluoro-3,6-dioxa-4-methyl-7-octene sulfonyl fluoride, converted to either the proton (H+), or the metal salt form.

Further preferred are sulfonated polymers and copolymers, such as sulfonated polymers of styrene and styrene/divinylbenzene, such as Amberlyst™ of Rohm and Haas, as well as sulfated silicas, aluminas, titania and/or zirconia; sulfuric acid-treated silica, sulfuric acid-treated silica-alumina, acid-treated titania, acid-treated zirconia, heteropolyacids supported on zirconia, heteropolyacids supported on titania, heteropolyacids supported on alumina, heteropolyacids supported on silica, and amorphous SiAl.

Mixtures of two or more acid catalysts may also be used.

When present, the acid catalyst is preferably used in an amount of from about 0.01% to about 10% by weight of the reactants.

It is recognized to those skilled in the art that the use of base or acid catalysts can enhance the rates of non-concerted carbon-carbon bond forming condensation reactions (such as an aldol condensation) more than the rates of concerted carbon-carbon bond forming condensation reactions (such as a Diels Alder condensation).

The following examples are illustrative of some of the embodiments of the present invention. Other embodiments within the scope of the claims herein will be apparent to one skilled in the art from consideration of the description set forth herein. It is intended that the specification, together with the examples, be considered exemplary only, with the scope and spirit of the invention being indicated by the claims which follow.

EXAMPLES

Example 1

A 316L stainless steel double-ended cylinder having a volume of 150 cm³ and capable of withstanding working pressures up to 5000 psig (344 bar) was obtained from the Swagelok Company. The cylinder was filled with ⅔ volume of bio-oil derived from the thermo-catalytic conversion of biomass. Air or nitrogen was introduced into the cylinder to fill the remaining volume. Both ends of the cylinder were plugged and the cylinder was placed into a programmable oven wherein the thermal cycle was controlled by temperatures (room temp to 212° F. @ 5 deg/min, 213° F. to 450° F., 350° F. & 230° F. @ 5 deg/min, 1 hr @ 450° F., 350° F. and 230° F. After the cylinder was cooled to room temperature, it was opened at one end to relieve pressure build-up and the sample removed for analysis. The cylinder was weighed before and after the application of heat and no evidence of weight change was noted. Table 1 depicts the changes in $C_2$-$C_5$ oxygenates and $C_2$-$C_5$ hydrocarbons between the starting bio-oil and the converted bio-oils:

TABLE 1

| Species | Start Oil | N₂ - 230° F. | N₂ - 350° F. | N₂ - 450° F. |
|---|---|---|---|---|
| wt % $C_2$-$C_5$ as Ox's | 4.6 | 3.3 | 3.0 | 2.2 |
| wt % $C_2$-$C_5$ as C's | 3.1 | 2.2 | 2.0 | 1.4 |

Table 2 represents the gas chromatography/mass spectrometry analysis of the starting bio-oil and the heated samples:

TABLE 2

| | Start Oil | N₂ - 230° F. | N₂ - 350° F. | N₂ - 450° F. |
|---|---|---|---|---|
| Oxygenates | | | | |
| Furans | 1.91 | 1.80 | 1.48 | 1.57 |
| Aldehydes | 1.15 | 0.63 | 0.41 | 0.53 |
| Ketones | 3.35 | 2.62 | 2.50 | 1.51 |
| Carboxylic Acids | 0.33 | 0.59 | 0.88 | 0.76 |
| Phenols | 16.06 | 15.80 | 15.48 | 14.97 |
| Indenols | 1.17 | 0.83 | 0.21 | 0.08 |
| Diols | 2.59 | 2.50 | 1.65 | 1.35 |
| Naphthols | 0.43 | 0.28 | 0.21 | 0.24 |
| Hydrocarbons | | | | |
| BTEX | 4.51 | 4.48 | 4.38 | 4.04 |
| Other Polyaromatics | 0.60 | 0.55 | 0.52 | 0.54 |
| Other Alkyl Benzenes | 1.32 | 1.32 | 1.16 | 1.20 |
| Indenes | 1.65 | 1.57 | 1.26 | 1.32 |
| Indanes | 0.17 | 0.19 | 0.18 | 0.18 |
| Naphthalenes | 1.09 | 1.11 | 1.04 | 1.15 |

The majority of ketones, aldehydes and carboxylic acids in Table 2 were $C_3$-$C_5$ oxygenates. Tables 1 and 2 illustrate the decrease in $C_3$-$C_5$ oxygenates in the condensation reactor product after heat treatment. In contrast, the other compound classes were essentially unaffected by treatment in the condensation reactor.

Example 2

A double-ended cylinder described in Example 1 was filled with ⅔ volume of a naphtha fuel stream. Nitrogen was introduced into the cylinder to fill the remaining volume. Both ends of the cylinder were plugged and the cylinder was placed into a programmable oven wherein the thermal cycle was controlled from 213° F. to 450° F. @ 5 deg/min and then 1 hr @ 450° F. After the cylinder was cooled to room temperature, it was opened at one end to relieve pressure build-up and the sample removed for analysis. The cylinder was weighed before and after the application of heat and no evidence of weight change was noted. The gc/ms data of the starting naphtha and the naphtha following completion of heating is set forth in Table 3. The majority of ketones, aldehydes and carboxylic acids in Table 3 were $C_3$-$C_5$ oxygenates. Table 3 illustrate the decrease in $C_3$-$C_5$ oxygenates in the condensation reactor after heat treatment.

TABLE 3

| | Start Naphtha | Reacted Naphtha |
|---|---|---|
| Oxygenates: | | |
| Aldehydes | 2.13 | 1.17 |
| Furans | 1.51 | 1.30 |
| Ketones | 11.90 | 9.10 |
| Carboxylic Acids | 0.21 | 0.30 |
| Phenols | 1.67 | 1.27 |
| Hydrocarbons: | | |
| BTEX | 64.32 | 64.51 |
| Other Benzenes/Toluenes | 7.21 | 5.14 |
| Indenes | 1.05 | 0.74 |
| Indanes | 0.58 | 0.46 |
| Naphthalenes | 0.14 | 0.11 |

From the foregoing, it will be observed that numerous variations and modifications may be effected without departing from the true spirit and scope of the novel concepts of the invention.

What is claimed is:

1. A process for producing a renewable biofuel from a liquid bio-oil or liquid pyrolysis oil, the process comprising:
   (a) introducing effluent from a biomass conversion unit into a separator and separating from the effluent a liquid bio-oil or pyrolysis oil;
   (b) subjecting carbonyl containing oxygenates within the separated liquid bio-oil or pyrolysis oil to a carbon-carbon bond forming condensation reaction in a condensation reactor to form $C_6$+ enriched condensates, wherein the carbonyl containing oxygenates are selected from the group consisting of $C_3$ oxygenates, $C_4$ oxygenates and $C_5$ oxygenates and mixtures thereof and further wherein the $C_3$, $C_4$ and $C_5$ oxygenates are selected from the group consisting of carboxylic acids, carboxylic acid esters, ketones and aldehydes;
   (c) contacting the bio-oil or pyrolysis oil containing condensates of step (b) with hydrogen and hydrotreating the $C_6$+ condensates to form a hydrotreated bio-oil or pyrolysis oil comprising $C_6$+ enriched hydrocarbons; and
   (d) removing the hydrotreated bio-oil or pyrolysis oil comprising $C_6$+ enriched hydrocarbons from the hydrotreater and fractionating the hydrotreated bio-oil or pyrolysis oil comprising $C_6$+ enriched hydrocarbons to obtain a $C_6$+ renewable biofuel.

2. The process of claim 1, wherein the condensation reactor in step (b) is a distillation column.

3. The process of claim 2, wherein condensation in the distillation column occurs in the presence of a heterogeneous acid catalyst.

4. The process of claim 3, wherein the heterogeneous acid catalyst is selected from the group consisting of organic sulfonic acids; perfluoroalkylsulfonic acids; zeolites; sulfated transition metal oxides, and perfluorinated ion exchange polymers containing pendant sulfonic acid, carboxylic acid, or sulfonic acid groups; sulfonated copolymers of styrene and divinylbenzene; sulfated silicas, aluminas, titania and/or zirconia; and amorphous SiAl and mixtures thereof.

5. The process of claim 4, wherein the heterogeneous acid catalyst is selected from the group consisting of ZSM-type zeolites, zeolite beta, sulfonated fluoropolymers or copolymers, sulfated zirconia and amorphous SiAl.

6. The process of claim 5, wherein the heterogeneous catalyst is a zeolite beta.

7. The process of claim 3, wherein the heterogeneous acid catalyst is located in the distillation column at a pre-determined location within the distillation column.

8. The process of claim 1, wherein the carbon-carbon bond forming condensation reaction is a Diels-Alder reaction.

9. The process of claim 8, wherein the condensation reactor is a distillation column.

10. The process of claim 1, wherein the $C_6+$ enriched condensates are prepared in step (b) by an aldol condensation reaction.

11. The process of claim 1, wherein the $C_6+$ enriched condensates are prepared in step (b) by a Michael addition reaction.

12. The process of claim 1, wherein the $C_6+$ enriched condensates are prepared in step (b) by a Robinson annulation reaction.

13. The process of claim 1, wherein the ketones are methyl vinyl ketone and ethyl vinyl ketone.

14. The process of claim 1, wherein the $C_6+$ enriched hydrocarbons of step (c) are separated into a naphtha fraction containing predominately $C_5$ through $C_{10}$ hydrocarbons and a hydrocarbon fraction containing $C_{10}+$ hydrocarbons.

15. A process for enhancing the yield of either hydrotreated bio-oil from a liquid bio-oil stream or hydrotreated pyrolysis oil from a liquid pyrolysis stream, the liquid bio-oil stream or liquid pyrolysis stream containing oxygenates selected from the group consisting of $C_3$ oxygenates, $C_4$ oxygenates and $C_5$ oxygenates and mixtures thereof wherein the $C_3$, $C_4$ and $C_5$ oxygenates are selected from the group consisting of carboxylic acids, carboxylic acid esters, ketones and aldehydes, the process comprising:
(a) subjecting the $C_3$, $C_4$ and $C_5$ oxygenates within the liquid bio-oil stream or liquid pyrolysis stream to a carbon-carbon bond forming condensation reaction in a condensation reactor to produce $C_6+$ oxygenates;
(b) removing the $C_6+$ oxygenates from the condensation reactor and introducing them to a hydrotreater; and
(c) hydrotreating the $C_6+$ oxygenates to render $C_6+$ enriched hydrocarbons, wherein the amount of oxygen removed from the $C_6+$ oxygenates in the hydrotreater is from 90 to about 99.99%.

16. A process for producing a renewable biofuel from a hydrotreated bio-oil, the process comprising:
(a) feeding a liquid bio-oil stream to a distillation column;
(b) subjecting lower carbon oxygenates in the liquid bio-oil stream to a carbon-carbon bond forming condensation reaction in the distillation column and forming $C_6+$ oxygenates from the lower carbon oxygenates, wherein the lower carbon oxygenates are selected from the group consisting of $C_3$ oxygenates, $C_4$ oxygenates and $C_5$ oxygenates and mixtures thereof and further wherein the $C_3$, $C_4$ and $C_5$ oxygenates are selected from the group consisting of carboxylic acids, carboxylic acid esters, ketones and aldehydes;
(c) removing the $C_6+$ oxygenates from the distillation column and introducing them into a hydrotreater;
(d) hydrotreating the $C_6+$ oxygenates in the hydrotreater to render $C_6+$ enriched hydrocarbons; and
(e) subjecting the $C_6+$ enriched hydrocarbons to fractionation to render a 180° F.-420° F. naphtha and at least one hydrocarbon fraction having a boiling point less than 180° F.

17. A process for producing a renewable biofuel from biomass, the process comprising:
(a) separating a predominately organic liquid bio-oil phase from treated biomass, wherein the organic liquid bio-oil phase comprises oxygenates selected from the group consisting of $C_3$ oxygenates, $C_4$ oxygenates and $C_5$ oxygenates and further wherein the $C_3$, $C_4$ and $C_5$ oxygenates are selected from the group consisting of carboxylic acids, carboxylic acid esters, ketones and aldehydes;
(b) forming $C_6+$ oxygenates through a carbon-carbon bond forming reaction from the $C_3$ oxygenates, $C_4$ oxygenates and $C_5$ oxygenates in the organic liquid bio-oil phase;
(c) introducing the $C_6+$ oxygenates into a hydrotreater and hydrotreating the $C_6+$ oxygenates in the hydrotreater to produce $C_6+$ enriched hydrocarbons; and
(d) subjecting the $C_6+$ enriched hydrocarbons to fractionation to render separate hydrocarbon fractions containing (i) $C_5$ to $C_{10}$ hydrocarbons and (ii) $C_{10}+$ hydrocarbons.

18. The process of claim 17, wherein the hydrotreater has a catalytic bed.

19. The process of claim 17, wherein transportation fuels are prepared from the separated hydrocarbon fractions of step (d).

20. The process of claim 17, wherein the $C_3$ oxygenates, $C_4$ oxygenates and $C_5$ oxygenates include methyl vinyl ketone and ethyl vinyl ketone.

21. The process of claim 17, wherein the $C_6+$ oxygenates of step (b) are prepared through an aldol condensation reaction, a Diels-Alder reaction, a Michael addition, or a Robinson annulations reaction or a mixture thereof.

22. The process of claim 17, wherein the $C_6+$ oxygenates of step (b) are prepared through a Diels-Alder reaction.

23. The process of claim 1, further comprising recovering solids from the effluent in step (a), regenerating the recovered solids and then introducing the regenerated solids into the biomass conversion unit.

24. The process of claim 1, further comprising recovering solids from the effluent in step (a), regenerating the recovered solids, introducing the regenerated solids to a biomass feedstream and then introducing the biomass feedstream into the biomass conversion unit.

* * * * *